United States Patent [19]

Schultz

[11] Patent Number: 4,602,517

[45] Date of Patent: Jul. 29, 1986

[54] FLUID SAMPLING METHOD AND APPARATUS

[76] Inventor: Harold R. Schultz, P.O. Box 10030, Reno, Nev. 89520

[21] Appl. No.: 700,285

[22] Filed: Feb. 11, 1985

[51] Int. Cl.[4] .............................................. G01N 1/14
[52] U.S. Cl. .............................. 73/864.16; 73/863.32; 73/864.14
[58] Field of Search ........... 73/863.32, 864.14, 864.16, 73/864.17, 864.18; 422/100

[56] References Cited

U.S. PATENT DOCUMENTS

| | | | |
|---|---|---|---|
| 3,327,535 | 6/1967 | Sequeira | 73/863.32 |
| 4,106,911 | 8/1978 | Marcelli | 73/863.32 |
| 4,406,170 | 9/1983 | Kuhn | 73/864.18 |
| 4,459,864 | 7/1984 | Cirincione | 73/863.32 |
| 4,478,094 | 10/1984 | Salomaa | 73/863.32 |
| 4,539,854 | 9/1985 | Bradshaw et al. | 422/100 X |

Primary Examiner—Stewart J. Levy
Assistant Examiner—Tom Noland
Attorney, Agent, or Firm—Herbert C. Schulze

[57] ABSTRACT

This is a method and apparatus for fluid sampling, particularly fluid sampling of like quantities of similar fluids, particularly in small quantities for testing and analysis. The apparatus and the method comprises the sampling and simultaneous sampling of a variety of dissimilar fluids in identical quantitative amounts. The method involves the extraction of samples of the various fluids to be analyzed and the dispensing of such fluid samples by activation of a single control lever wherein the lever can be used to extract in defined quantities by movement to a stop position or wherein the quantity may be selected at infinite quantity measurements.

1 Claim, 8 Drawing Figures

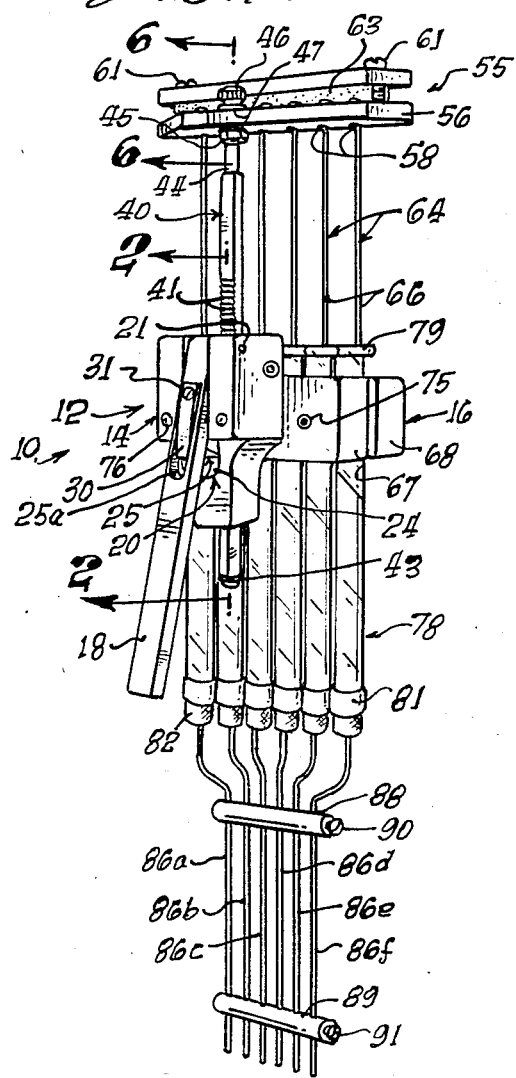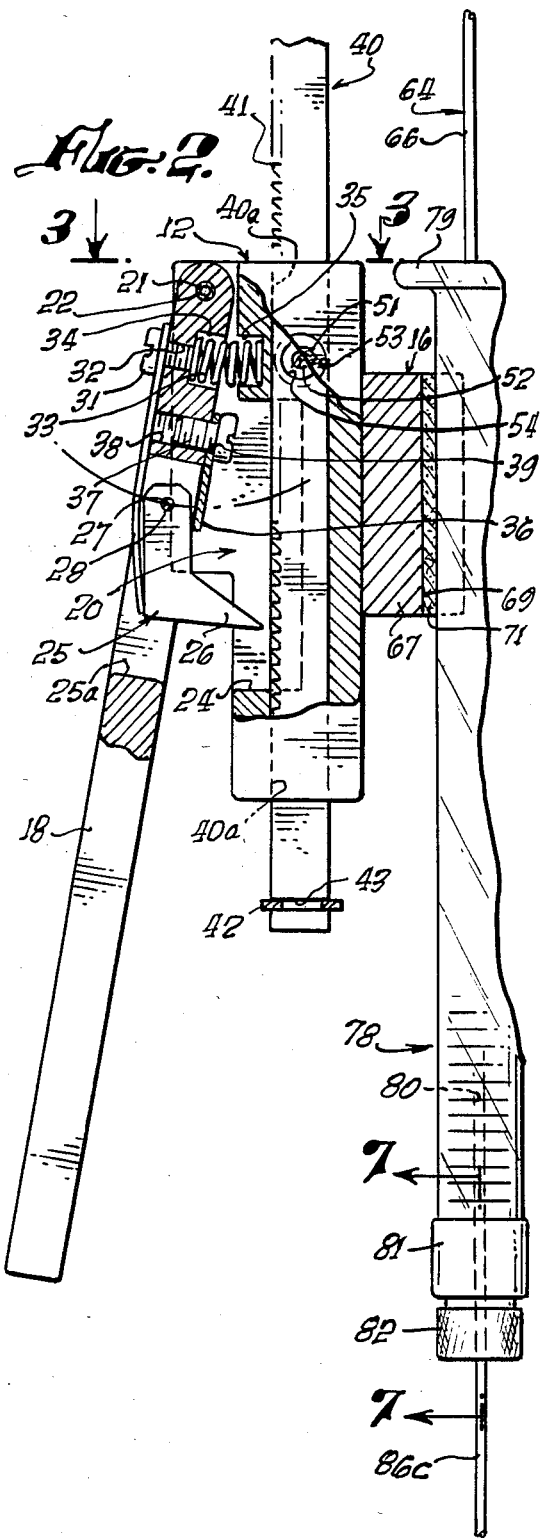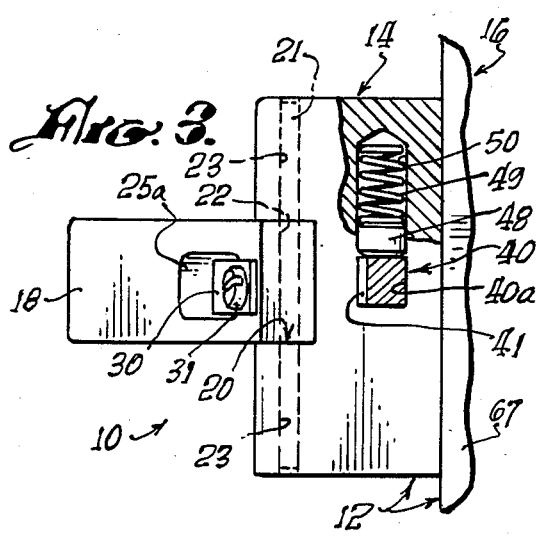

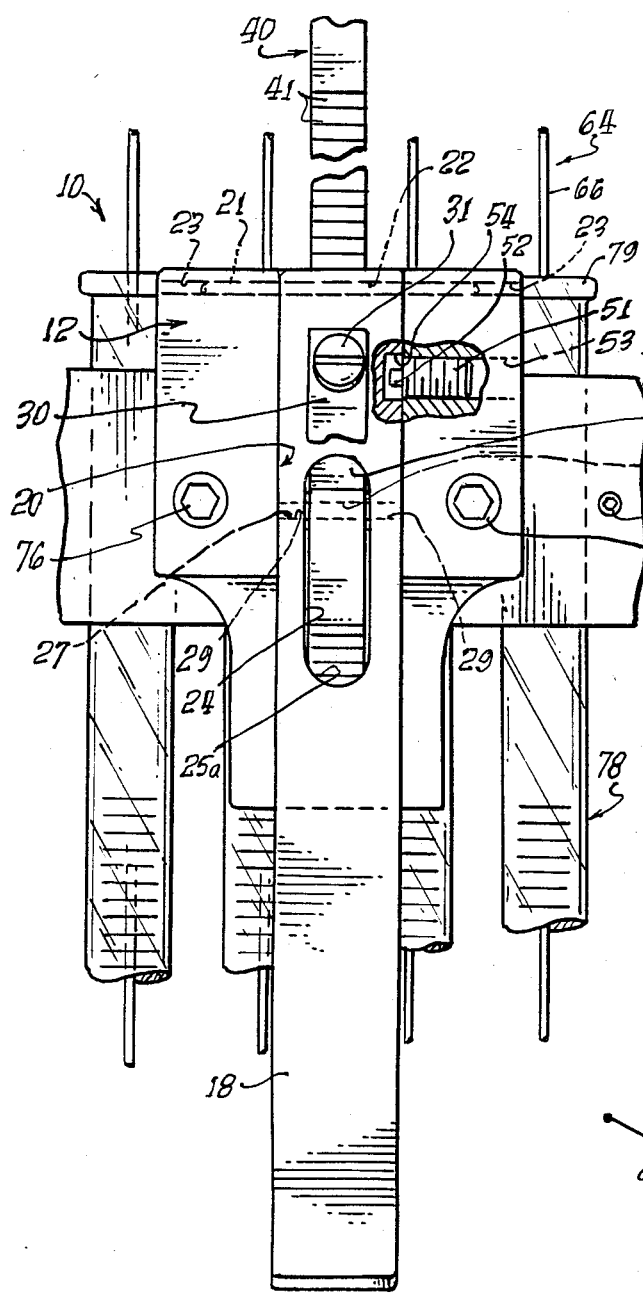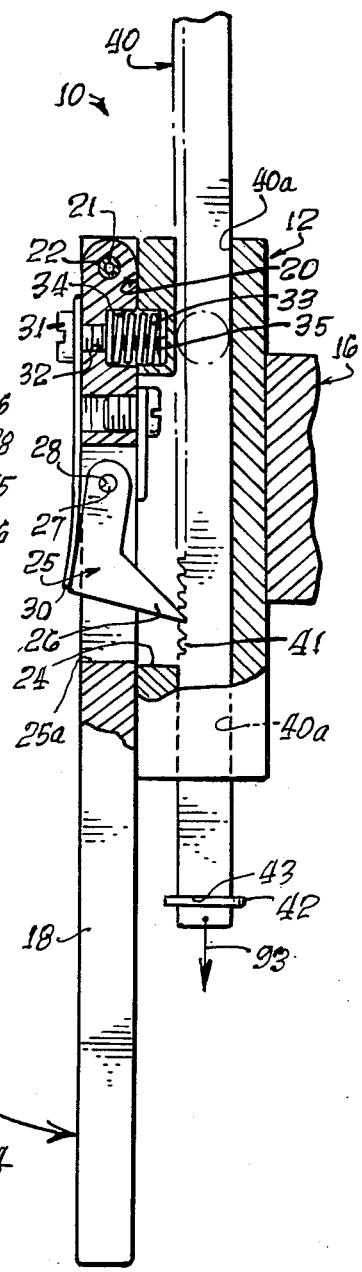

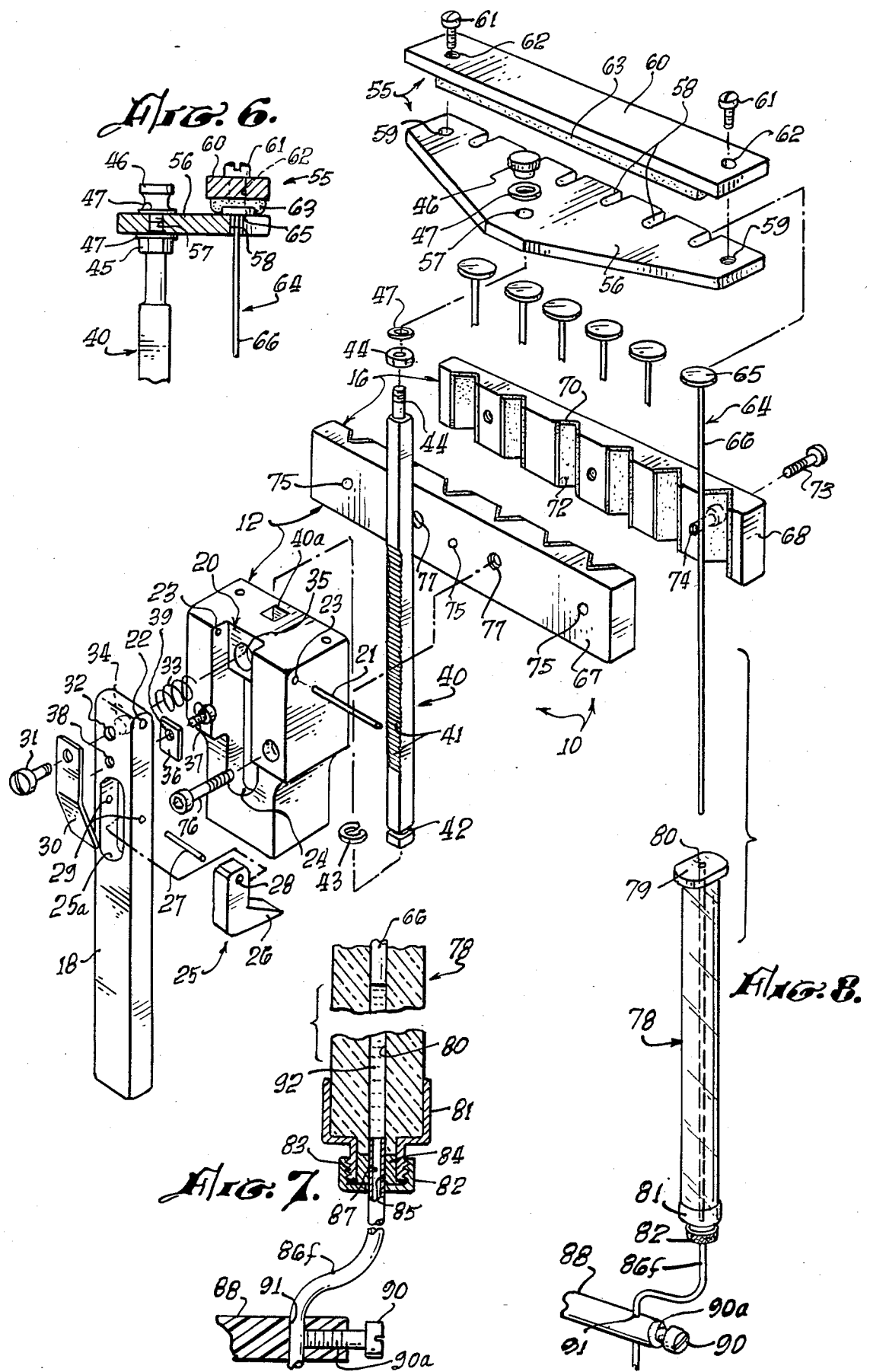

FLUID SAMPLING METHOD AND APPARATUS

CROSS REFERENCE TO RELATED PATENT APPLICATIONS

There are no related applications pending related to this invention, except my application for design patent on "SYRINGE DISPENSER" filed concurrently herewith.

BACKGROUND OF THE INVENTION

1. Field of the Invention

This invention is in the general field of analysis of fluid samples; the invention is more particularly directed to a method and apparatus for the gathering and extraction of one or more like quantities of similar or dissimilar fluids for analysis;

The apparatus is further directed towards such a method and apparatus as has been described wherein by a single actuation the correct amount of fluid is collected from each of one or more different samples.

2. Description of the Prior Art

There have been many methods and apparatus devised for the collection of fluid samples in the past. To recite them would be unnecessarily cumbersome and almost impossible since various laboratories and the like have used various techniques.

However, until this time there has not been a satisfactory method and apparatus by which exact quantities of similar or dissimilar fluids may be extracted simultaneously for complete analysis, and wherein the quantity is indefinitely and infinitely controlable.

The present invention is therefore unique in providing a method and apparatus for the simultaneous extraction and dispensing of identical quantities of one or more similar or dissimilar materials for thorough analysis.

SUMMARY OF THE INVENTION

This invention has been brought about by the increasing (almost on a daily basis) advances in medical and other sciences wherein fluids are utilized as the medium from which various data and information may be obtained by analysis.

It has been quite common in the past to extract from a syringe or the like a fixed quantity of fluid of analysis as to its components.

It has also been quite common to extract multiple numbers of different fluids, each requiring an exact measured relationship. This has been a cumbersome and difficult problem in the past.

I have been involved in a study of this problem for a long period of time and have now conceived and completely developed a method and apparatus which has heretofore been unthought of, and unknown, whereby one fluid, or a multiplicity of fluids, may be tested, experimented with, and otherwise used in identical quantities from a single actuating device which insures absolute accuracy of each measurement. With my method and apparatus a single measurement, or multiple measurements, can not be at variance with the desired exact quantity or quantities. In the present method and apparatus it is possible to have numerous identical (in quantity) samples regardless of their nature, with complete accuracy.

Furthermore in the present invention exact accuracy may so be obtained so that all of the samples desired for any particular test may be exactly of the quantity desired.

I have achieved this end by mounting the appropriate number of extracting devices in the nature of the vacuum lifting pumps together with appropriate intake arrangements which will not allow leakage. Each of the devices is equipped with a lifting piston within a cylinder whereby when each of the desired samples is encountered by the intake conduit, each will receive a specific and exact quantity upon a single movement of the actuating lever. Likewise, when the fluid is dispensed it will be dispensed in equal quantities.

It is an object of this invention to provide a method and apparatus by which samples of fluids may be accurately and equally extracted from their basic mediums for analysis.

It is another object of this invention to provide such a device as is herein described wherein one actuation extracts the same amount of fluid from one container, or a number of different containers.

Another object of this invention is to expell equal quantities of fluids for analysis by a single actuation of a single element.

The foregoing and other objects and advantages of this invention will become apparent to those skilled in the art upon reading the following description of a preferred embodiment in conjunction with the appended drawings.

BRIEF DESCRIPTION OF THE DRAWINGS

FIG. 1 is a perspective of a preferred embodiment of an apparatus to practice the method of this invention;

FIG. 2 is an enlarged, partially broken away, partially sectioned view on 2—2 of FIG. 1;

FIG. 3 is an enlarged, partially broken away, partially sectioned view on 3—3 of FIG. 2;

FIG. 4 is a fragmentary partial front elevation of the device of FIG. 1 with certain parts broken away;

FIG. 5 is a view similar to a portion of FIG. 2, but showing the actuating advancing mechanism in another position;

FIG. 6 is an enlarged fragmentary partially sectioned view on 6—6 of FIG. 1;

FIG. 7 is an enlarged, partially broken away, partially sectioned view on 7—7 of FIG. 2; and FIG. 8 is an exploded perspective of the various components of the various portions of the device of FIG. 1.

DESCRIPTION OF A PREFERRED EMBODIMENT

As viewed in FIG. 1, the multiple syringe dispenser generally shown by the reference numeral 10 comprises a general central lock assembly 12, an actuator assembly 17, and a two clamp assembly 16.

Referring particularly to FIGS. 1, 2, and 3 there is shown a handle 18 which is pivotally supported by means of pin 21 within the slot 20 of the central block assembly 12. The pivot pin 21 passes through an aperture 22 in handle 18 and is thrust into corresponding openings 23 on either side of the slot 20 within block 12. The slot 20 extends through the block 12 at an extension thereof 24. This extension 24 of the slot 20 permits the movement of a pawl member 25 to allow the paul member to come into contact with a drive rod described later in this description. The pawl member 25 is pivotally mounted between side walls of a slot 25a located in the handle 18. A pivot pin 27 passes through a hole 28 in an upwardly extending arm portion of the pawl 25 and through holes 29 (see FIG. 8) located in the handle 18. A pointed offset portion of the pawl 25 is shown as a triangular portion 26 as viewed in FIG. 2. A float spring 30 is affixed to the handle by a screw 31 threaded into a threaded opening 32 in the handle 18. A coil spring 33 is placed between the receiving recesses 34 in the handle 18 and aligned receiving opening 35 in the main portion of the block 12. A stop tab 36 is shown affixed to the inner side of the handle 18 and projects downwardly over a portion of the slot 25a in order to keep the pawl member 25 from moving too far in a right hand direction as viewed in FIG. 2. The screw 37 fits into threaded opening 38 in the handle 18 by passing through an opening 39 in the stop tab 36.

The handle 18 associated with its pawl 25 provides an advancing means for intermittently moving a drive rod 40 a designated amount of each actuation of the handle 18. This action is shown in FIGS. 4 and 5 wherein the pawl has contacted the rod 40 at its forward face formed with serations or teeth 41. These serations are spaced at equal distances from one another in order to allow an accurate equal stroke of the drive rod 40 in its dispensing operation. The drive fits into a similarly shaped rectangular opening 40a running the full length from top to bottom of the member 12 and coming into contact with the deepened slot portion 24 of the slot 20. Upward limit of the movement of the drive rod 40 is accomplished by providing a retaining ring 42 which is shown riding in slot 43 in the drive rod 40.

The upper end of the drive rod 40 is shown having a reduced portion culminating in a threaded shank 44 as is indicated in the section of FIG. 6 and the exploded view of FIG. 8. An adjustment nut 45 along with spacer washers 47 allow the drive to be mounted to syringe plunger support assembly with the aid of a tightening nut 46.

Referring now to FIG. 3 it can be seen that there is a frictional pad 48 being applied to a side face of the drive rod 40 in order to prevent inadvertent movement of rod 40 through the block member 12. This pad 48 is urged toward the drive rod 40 by means of a spiral spring 49 mounted in recess 50. The recess 50 is formed in the block 14 in order to accommodate the spring 49.

The handle 18 is restricted from moving outwardly beyond a desired location by means of a threaded member 51 mounted in a threaded opening 53 in the block 12 and having a projection 52 at one end of the screw 51 which extends into a limit recess 54 in the handle 18 (FIG. 4).

The syringe plunger support assembly designated by the reference numeral 55 comprises a lower plate 56 to which the drive rod member is affixed as previously described. An opening 57 is provided for this purpose. As best seen in FIG. 8 slots 58 allow the insertion of the plunger members 64 later to be described. Threaded openings 59 are formed at the outer ends of the plate 56 to accommodate the screws 61 passing through opening 62 in an upper plate 60. A cushioning pad 63 extends the length of the plate 60 in order to provide a frictional pressure onto enlarged disk like ends 65 of the plunger means. In the particular configuration illustrated there is provision for 6 such plunger assemblies. It is understood that more or less, including any practical number from 1 upward could be used.

Tube clamping assembly 16 is shown to comprise block members 67 and 68. Referring again to FIG. 8 it can be seen that a number of "V" shaped slots 69 in the block 67 are in alignment with "V" shaped slots 70 in block 68. Protective friction pads 71 and 72 are affixed to the "V" shaped slots in order to more delicately grip the handles of the syringe tubes as will be described later. Screws 73 passing through openings 74 in the block 68 are threaded into threaded openings 75 in block 67 in order to clamp the two members together surrounding the syringe tubes. The tubes 78 have flat-like upper flange portions 79 and the tubes have a longitudinal cylinder openings 80 through the entire length of the tubes 78.

As shown in the enlarged fragmentary seciton in FIG. 7, the plunger 66 fits into the cylinder 80 and can force out any liquid trapped in the chamber 80 upon actuation. The syringe 78 is provided with a lower cap member 82 which retains a plug 84. Each plug 84 is provided with an opening 85, each of which accepts one hollow tubular extension 86a, 86b, 86c, 86d, 86e, and 86f.

It is to be noted that in FIG. 1 and 8 these hollow tubular members 86a through 86f are configured to be brought together to closer proximity to one another and to be passed through openings in spacer members 88 and 89. Each of the members 86a through 86f is formed with an inner passage 87 as seen in FIG. 7. Screws 90 and 91 are threaded into threaded openings 90a and 91a and retain at least one of the members 86 from movement. In this manner all of the tubular members 86a through 86f are maintained in proper physical relationship to one another.

When it is desired to fill the syringes with fluid, the ends of the rods 86a through 86f are inserted into the appropriate fluid or fluids. By raising the assembly 55 fluid will be pulled through the tubes and into the individual syringes. When they are filled either completely or to a desired partial position, the fluid will be retained within the syringes and tubes 86a through 86f. This is naturally so as will be understood by those skilled in the art since the diameter of the tubes is extremely small.

When it is desired to have the fluid 92 dispensed, this is accomplished in a regulated and metered manner when the drive rod is advanced in the direction of arrow 93 as viewed in FIG. 5. This advancement is effected by moving the handle 18 in the direction of arrow 94 also illustrated in FIG. 5. With each actuation of the handle 18 the drive rod is moved an exact distance and simultaneously moves the plunger 64 of each of the syringe assemblies through the conduit 80 within the syringe, dispensing a given amount of fluid from the cylindrical chamber within the syringe.

While the embodiment of this invention as shown and described, both in method and apparatus, is fully capable of achieving the objects and advantages desired, it is to be understood that such embodiment is for purposes of illustration and not for purposes of limitation, and particularly the number of dispensing syringes which can be so utilized is not in any manner restricted to the number illustrated and may be any reasonable and convenient number desired.

I claim:

1. A fluid extracting and dispensing apparatus comprising in combination: syringe body carrying means; syringe body carried by such syringe body carrying means; syringe piston rod means located within said syringe body and extending a distance outwardly therefrom from a first enlarged end exterior of said syringe body and movable therein; movable piston rod gripping means gripping said enlarged end of said piston rod and comprising a first plate having slot means suitable to accommodate the piston rod with the enlarged portion resting upon said first plate; a second plate having a resilient member affixed thereto wherein said first and second plates are held together with the resilient member pressing the enlarged end of said piston rod downward against said first plate exterior of said syringe body; actuating rod means attached to said piston rod gripping means and slidably mounted in actuating lever means frame attached to the syringe body carrying means; movable actuating lever means pivotally mounted upon said lever means frame and including spring means limiting the said movable lever means motion in actuating travel and wherein spring means returns said lever means to an original starting position upon release of pressure; pawl means carried by said lever means, said pawl means being cooperable with said actuating rod means in such manner as to be capable of imparting movement to said actuating rod means in one direction when said lever means is moved; and tubular extension means attached to a second end of said syringe body.

* * * * *